United States Patent [19]

Wong et al.

[11] Patent Number: 6,083,747
[45] Date of Patent: Jul. 4, 2000

[54] METHOD OF PREPARING HEMATOPOIETIC STEM CELLS WITH GP105-SPECIFIC ANTIBODIES

[75] Inventors: Peter M. C. Wong; Siu-Wah Chung, both of Gladwyne, Pa.; Xiaodong Han, San Francisco, Calif.

[73] Assignee: Stemcell Therapeutics LLC, Bala Cynwyd, Pa.

[21] Appl. No.: 09/114,146

[22] Filed: Jul. 13, 1998

Related U.S. Application Data

[63] Continuation-in-part of application No. 08/471,188, Jun. 6, 1995.

[51] Int. Cl.[7] ........................................ C12N 5/00
[52] U.S. Cl. ............................ 435/325; 435/2; 435/378
[58] Field of Search ........................... 435/7.1, 325, 7.21, 435/2, 378; 530/387.1, 388.2, 388.1, 388.22, 412, 413; 424/140.1

[56] References Cited

PUBLICATIONS

Spangrude & Johnson, *PNAS* 87:7433–7437 (1990).
Spangrude, et al., *Blood* 78:1395–1402 (1991).
Spangrude, et al., *Science* 241:58–62 (1988).
Molineaux, et al., *Exp. Hematol.* 14:710 (1986).
Nakahata & Ogawa, *PNAS* 79:3843–3847 (1982).
Wong et al., *Immunity* 1:571–583 (1994).
Orlic et al., *Blood* 82:762–770 (1993).
Jordan, et al., *Science* 252:953–963 (1990).
Smith, et al., *PNAS* 88:2788–2788–2792 (1991).
Omary et al., "Human Cell–Surface Glycoprotein with Unusual Properties", *Nature*, vol. 286, No. 28, Aug. 1980, pp. 888–891.
Karasuyama et al., "A Complex of Glycoproteins is Associated with $V_{pre}\beta/\lambda_5$ Surrogate Light Chain on the Surface of μ Heavy Chain–Negative Early Precursor B Cell Lines", *J. Exp. Med.*, vol. 178 Aug. 1993, pp. 469–478.
Krause et al., "Characterization of Murine CD34, a Marker for Hematopoietic Progenitor and Stem Cells", *Blood*, vol. 84, No. 3, Aug. 1994, pp. 691–701.
Han et al., "Identification of a Unique Membrane–Bound Molecule on a Hemopoietic Stem Cell Line and on Multipotent Progenitor Cells", *Proc. Natl. Acad. Sci.*, vol. 92, Nov. 1995, pp. 11014–11018.
Matthews et al., *Cell* 65:1143–1152 (1991).
Sposi et al., *PNAS* 89:6353–6357 (1992).
Chung et al., *PNAS* 86:7957–7960 (1989).
Shigeno et al., *Lancet* ii:320–323 (1968).
Raff et al., *Nature* 230:50–51 (1971).
Dexter et al., *Nature* 277:471–474 (1979).
Chung et al., *PNAS* 88:1585–1589 (1991).
Wong et al., *PNAS* 83:3851–3854 (1986).
*Antibodies: A Laboratory Manual*, Harlow et al. Cold Spring Harbor Publications, p. 726 (1988).
Geyson et al., *J. Immunol. Methods* 102:259–274 (1978).
Cuatvecasos, *J. Biol. Chem.* 245:3059 (1970).

*Primary Examiner*—Christina Y. Chan
*Assistant Examiner*—Phillip Gambel
*Attorney, Agent, or Firm*—Foley & Lardner

[57] ABSTRACT

An N-glycosylated glycoprotein, having the molecular weight of 105 kDa when glycosylated and 85 kDa when non-glycosylated, is present on the surface of BL3 hematopoietic stem cells, but is absent from the surfaces of other cells including 32D and FDC-P1 myeloid progenitor cells, EL4 T-cells and 3T3 fibroblasts. Antibody which binds the gp105 protein inhibits the proliferation of BL3 cells that occurs in BL3-conditioned medium (BL3CM). It also can inhibit preferentially the formation of fetal liver cell-derived, multi-lineage colonies in vitro, and the development of bone marrow cell-derived, spleen colony-forming unit foci in vivo. Anti-gp105 antibody can be employed in making a preparation that is enriched for hematopoietic stem cells. Substantially purified from other proteins, the gp105 protein itself is a useful reagent for isolating and characterizing the factor(s) responsible for the proliferative effect of BL3CM.

1 Claim, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (xi) SEQUENCE DESCRIPTION: SEQ ID NO:1:

GAATTCTGAC ACCTCGTCTG TGCTCCATTT GGAAACTCTA CTAGCTGGGA TACCCAGACA      60

GTCGGAAGAA GCTTGCTCTG CTGCTCCCAG CGCAAGGGCA GACACGGAAT GGGAGGCTTA     120

AAGGAGAGAA ATACTGCTGA GCGTCGCTGG GCCTGCTGCT GGGTCTGGGC TTGCTGCTGG     180

GTGGGCTGAG CTGTTGAACC TGCTGAGGCT GTTGGACGGG TGGGGCCTGC TTGAGGCTGC     240

TGGGCCTGCT GGGGCTGCTG GGCCTGCTGA GCCTGTGGAG CCTGCTGGGC CTGCTGGACT     300

GTGGCGCCTG CTGGGCTGCT GGACCTGTGG CGCCTGCTGG GCTGTGGAGT CTGTGGGCC     360

TGTGGAGCCT GCGGGCCTGC TGGGCTTGCT GGGCCTGCTG GCTCGGACGT                410

METHOD OF PREPARING HEMATOPOIETIC STEM CELLS WITH GP105-SPECIFIC ANTIBODIES

This is a continuation-in-part of application Ser. No. 08/471,188, filed Jun. 6, 1995, pending.

The present invention was made in part with funds provided by the National Institutes of Health under NIH grants DK41298 and HL46547.

BACKGROUND OF THE INVENTION

The present invention relates to gp105, a N-glycosylated glycoprotein substantially purified from other proteins that has a glycosylated molecular weight of 105 kDa and a non-glycosylated molecular weight of 85 kDa, and that is present on the surface of BL3 hematopoietic stem cells but absent from those of other cells including 32D and FDC-P1 myeloid progenitor cells, EL4 T-cells and 3T3 fibroblasts. The invention further relates to methods of using antibody against gp105 to produce an enriched hematopoietic stem cell population.

All circulating blood cells develop from pluripotent stem cells through the process of hematopoiesis. Hematopoietic stem cells are undifferentiated cells capable of self-renewal and differentiation into committed progenitor cells of the myeloid, erythroid, megakaryocytic and lymphoid blood cell lineages. A thorough analysis of hematopoietic stem cells is fundamental to a comprehensive understanding of the developmental biology of the hematolymphoid system. Relatively little is known, however, about hematopoietic stem cells.

Functionally, hematopoietic stem cells are capable of long-term reconstitution of the hematolymphoid system of lethally-irradiated recipients in vivo. See Spangrude & Johnson, *PNAS* 87:7433–7437 (1990); Spangrude et al., *Blood* 78:1395–1402 (1991). They also can differentiate into pre-day 12 spleen colony-forming units (CFU-S), which can be observed in in vivo assays for spleen foci formation. See Spangrude et al., *Science* 241:58–62 (1988); Molineux et al., *Exp. Hematol.* 14:710 (1986); Nakahata & Ogawa, *PNAS* 79:3843–3847 (1982). In addition, hematopoietic stem cells develop a "cobblestone" morphology upon adherence in vitro to a layer of stromal cells. See Wong et al., *Immunity* 1:571–583 (1994).

Efforts to characterize hematopoietic stem cells in more detail have been hampered primarily because of the proportionately minute amount ($10^{-4}$ to $10^{-5}$) of hematopoietic stem cells as compared with all cells, even in blood cell-forming organs such as bone marrow or the fetal liver. See Orlic et al., *Blood* 82:762–770 (1993). Accordingly, the elucidation of physical characteristics unique to hematopoietic stem cells is desirable as a means to produce enriched stem cell populations. See, e.g., Spangrude et al., *Blood* 78:1395–1402 (1991). All known hematopoietic stem cell enrichment protocols involve cell-separation methods based on the selection for cell surface markers or genetic (retroviral) markers. See Jordan et al., *Science* 252:953–963 (1990). Although methods of producing enriched populations of hematopoietic stem cells have been described, the absence of unique markers has precluded the isolation of an unequivocally pure population of hematopoietic stem cells.

Hematopoietic stem cells express cell surface differentiation antigen (Thy-1) and stem cell antigen-1 (Sca-1). They do not, however, express the lineage markers (Lin) characteristic of B cells (B220), granulocytes (Gr-1), myelomonocytic cells (Mac-1) and T cells (CD4, CD8)). See Spangrude et al., supra. The reportedly most widely used hematopoietic stem cell enrichment protocol involves the use of monoclonal antibodies against Thy-1 and Sca-1. See Orlic et al., supra. Only a subset, however, of Thy-$1^+$, Sca-$1^+$ and Lin$^-$ cells are able to repopulate lethally-irradiated recipients long-term. See Smith et al., *PNAS* 88:2788–2792 (1991). Selection based on Thy-1 and Sca-1 expression thus does not produce a pure hematopoietic stem cells population. Similarly, other hematopoietic stem cell enrichment techniques such as those which involve the use of monoclonal antibodies against protein tyrosine kinases such as the W locus gene product, c-kit, and fetal liver kinase-2 (flk-2) apparently are unable to distinguish between hematopoietic stem cells and progenitor cells. See, e.g., Matthews et al., *Cell* 65:1143–1152 (1991).

The recent establishment of a cell line from a lethally-irradiated recipient mouse reconstituted with fetal liver cells previously transduced with a rearranged retroviral genome has been reported. See Wong et al., supra. BL3 cells exhibit all of the functional hematopoietic stem cell properties, i.e., they can reconstitute lethally-irradiated recipients long-term, they give rise to pre-CFU-S and colony-forming cells and they develop "cobblestones" upon association with stromal cells. In addition to being Thy-$1^+$, Sca-$1^+$ and Lin$^-$, BL3 cells also express a transcription factor, GATA-1, known to be expressed in hematopoietic stem cells. See Sposi et al., *PNAS* 89:6353–6357 (1992). Furthermore, BL3 cells are embryonic in origin, having derived from fetal liver cells of 12-day old mouse embryos. BL3 cells thus may possess different cell surface markers than adult hematopoietic stem cells. See Jordan et al., supra; Spangrude et al., supra.

The foregoing discussion reveals the need to identify other cell surface markers on hematopoietic stem cells, specifically to enable the production of more highly enriched hematopoietic stem cell populations, and generally to facilitate a better understanding of the growth and differentiation of immature blood cells.

SUMMARY OF THE INVENTION

Accordingly, an object of the present invention is the identification and isolation of a marker present on the cell surface of BL3 hematopoietic stem cells but not present on committed progenitor cells or mature blood cells, and the use of such a marker in turn to identify putative hematopoietic stem cell regulatory factors. Another object of the present invention is an antibody against a BL3 cell surface marker and its use to produce an enriched hematopoietic stem cell population.

These objectives are achieved by gp105, a N-glycosylated glycoprotein substantially purified from other proteins that has a glycosylated molecular weight of 105 kDa and a non-glycosylated molecular weight of 85 kDa, and that is present on the surface of BL3 hematopoietic stem cells but absent from those of other cells including 32D and FDC-P1 myeloid progenitor cells, EL4 T-cells and 3T3 fibroblasts. The objectives are further achieved by an antibody against gp105 and the use of the antibody to enrich for hematopoietic stem cells.

One embodiment of the invention provides methods of using antibody against gp105 to prepare a composition enriched for hematopoietic stem cells according to the invention, comprising the steps of (a) providing antibody that binds gp105, (b) immobilizing the antibody on a solid support such that the antibody retains its gp105-binding capability, then (c) bringing a mixed population of cells containing putative hematopoietic stem cells into contact with the antibody such that the stem cells adhere to the support, and (d) removing nonadherent cells, whereby a population enriched for hematopoietic stem cells remains adhered to the support.

Another embodiment of the invention provides a kit for preparing a composition enriched for hematopoietic stem cells, comprising an antibody that binds gp105, and further comprising written directions for the use of the kit.

A further embodiment of the invention provides methods for detecting in a sample a hematopoietic regulatory factor that binds gp105, comprising (a) contacting a sample suspected of containing said growth factor with labeled-gp105, and (b) detecting the binding of the hematopoietic regulatory factor with labeled-gp105.

Another embodiment of the invention provides a kit for the detection of a hematopoietic regulatory factor that binds gp105, comprising labeled-gp105, and further comprising written instructions for the use of the kit.

Yet another embodiment of the invention provides an isolated DNA molecule encoding gp105. A particular embodiment of the invention provides an isolated DNA molecule that encodes gp105.

DETAILED DESCRIPTION OF PREFERRED EMBODIMENTS

An N-glycosylated glycoprotein (gp105) has been discovered and substantially purified from other proteins. It has a glycosylated molecular weight of 105 kDa and a non-glycosylated molecular weight of 85 kDa. Gp105 is present on the surface of BL3 hematopoietic stem cells but absent from the surfaces of other cells, including 32D and FDC-P1 myeloid progenitor cells, EL4 T-cells and 3T3 fibroblasts. The establishment and maintenance of the BL3 hematopoietic stem cell line has been described in detail in Wong et al., *Immunity* 1:571–583 (1994), which is incorporated herein by reference.

Gp105 was characterized by western blot and isolated by immunoprecipitation, both using polyclonal antibody raised against BL3 cells. This polyclonal antibody was prepared according to the following procedure. One adult New Zealand female rabbit was injected with $1.2 \times 10^8$ BL3 cells intravenously and was boosted three weeks later with another dose of $1 \times 10^8$ cells. Ten days later, it was bled and 30 ml of blood were collected. Subsequently, the animal was boosted every 6–8 weeks. The blood was collected and left standing at room temperature for 4 hrs and transferred to 4° C. for overnight incubation. The next day, clear serum was collected, which was then heat-inactivated at 56° C. for 30 min and absorbed with 0.1 volume packed with WEHI-3 cells twice, 0.1 volume packed EL4 cells twice and 0.1 volume packed murine red blood cells once. WEHI-3 and EL-4 cells were chosen for absorption because they were negative for gp105 in western blot analysis. The absorptions were performed by rotating the tubes at room temperature for one hour. The absorbed serum was collected by centrifugation at 1,000 g for 10 min. For titer determination, $1 \times 10^4$ BL3 cells or WEHI-3 cells in a final 100 µl volume were incubated with or without various dilutions of antiserum, and in the presence of rabbit complement at predetermined optimal concentration, 1:15 (Low-Tox-M, Accurate Chemical & Scientific Co. N.Y.). After 45 min of incubation at 4° C., equal volume of 0.4% Trypan blue was mixed with treated cells and viability was determined. The serum tested positive by assay for specific complement-mediated cytotoxicity as described in Shigeno et al., Lancet ii:320–323 (1968) and Raff et al., *Nature* 230:50–51 (1971), which are incorporated herein by reference. In this way, the specific killing for WEHI-3 cells was 58% at 1:4 dilution of the antiserum before absorption, and was 0% at 1:4 dilution and 12% at 1:2 dilution after absorption; whereas the specific killing for BL3 cells ranged from 95% to 100% at all dilutions examined from 1:0 to 1:128 before and after absorption. Based on this assay, the anti-BL3 antiserum has a titer of 1:1,000, which is defined as the dilution at which 50% specific killing of BL3 cells occurred.

Gp105 was characterized by western blot assay according to the following procedure. BL3 cells were harvested, washed twice with PBS containing 2% fetal calf serum (FCS) and lysed in 10 µl lysis buffer containing 10 mM Tris-HCl, pH 8.0, 50 mM NaCl, 1% Triton X-100, 1 mM PMSF (phenylmethylsulfonyl fluoride), 1 mM EDTA and 2 µg/ml aprotinin. The lysate was placed on ice for 30 min and was then spun at 14,000 rpm for 5 min at 4° C. The supernatant was collected and mixed with 2× sample buffer that contains 100 mM Tris-HCl, pH 6.8, 2% glycerol, 0.02% bromophenol blue, 2% SDS and 2% 2-mercaptoethanol. The mixtures were boiled for 3–5 min before loading onto a 7% of SDS-PAGE gel. Biotinylated SDS-PAGE standards (BioRad, Richmond, Calif.) were used as molecular weight markers. Electrophoresis was carried out in the presence of Tris-Glycine buffer using Tall Mighty Small vertical slab gel unit (Model SE280, Hoeffer Scientific, San Francisco, Calif.). After electrophoresis, the gel was soaked in Tris-Glycine buffer containing 20% methanol for 30 min and the proteins were transferred in the presence of the same buffer onto the Immobilon PVDF transfer membrane (Millipore Co, Bedford, Mass.). The membrane was blocked for more than 60 min at room temperature with blocking solution (GIBCO-BRL, Gaithersburg, Md.) and incubated for another 60 min at room temperature with primary antibodies at a concentration of 5 µg/ml in blocking solution. IgG from all sera was purified through a rProtein G Agarose column (BRL, Gaithersburg, Md.). Next, the membrane was washed twice with washing solution containing 50 mM Tris-HCl, pH 7.5, 200 mM NaCl and 0.05% v/v Tween 20, 5 min for each time. It was then incubated with 1 µg/ml of the biotinylated goat anti-rabbit IgG in blocking solution (GIBCO-BRL) for 30 min at room temperature. After being washed twice with washing solution, the membranes were incubated with 1:2500 streptavidin-alkaline phosphatase conjugate (BMB) for 30 min at room temperature, followed by another 4 washes. They were then visualized by staining with Lumi-Phos 530 (BMB) and exposure to X-ray films.

Gp105 was isolated by immunoprecipitation according to the following procedure. Twenty million BL3 cells were harvested and washed twice with P2 buffer (PBS plus 2% FCS). The cell pellet was resuspended with 0.5 ml P2 buffer and incubated with 10 µg IgG for two hrs at 4° C. The cells were washed twice with P2 and lysed with the same lysis buffer as described for western blot. The cell lysates were placed on ice for 30 min, spun and the supernatants transferred into the tubes containing 40 µl Protein A-agarose suspension (50% volume swollen agarose, BMB). They were incubated for a further two hrs at 4° C. Complexes of antigen-antibody-protein A-agarose were collected and washed three times with lysis buffer. The pellets were resuspended with 40 µl of 2× sample buffer, boiled for 3 min and spun for 2 min at room temperature. Supernatants were collected and separated by 7% SDS-PAGE. The proteins were visualized as described for western blots.

Specific recognition by antiserum raised against BL3 cells suggests that gp105 has a biological function on hematopoietic stem cells. The cytotoxicity of this antiserum for BL3 cells in the presence of complement suggests that gp105 is a molecule present uniquely on BL3 cell surfaces. Western blot and immunoprecipitation analyses confirmed this. For western blot analysis, one million each of BL3 cells, EL4 T-cells, 32D myeloid progenitor cells and 3T3 fibroblasts were lysed in buffer, electrophoresed and blotted onto PVDF membrane filters, which were then incubated with either antiserum raised against gp105 or the preimmune serum. A band with a molecular weight of 105 kDa was present distinctly in lysates of BL3 cells only. For immunoprecipitation, twenty million BL3 cells were incubated with either antiserum raised against BL3 cells or preimmune serum before cell lysis, and the cell lysate was then incubated with protein A agarose. The complexes were washed and boiled to release the proteins, which were then analyzed as described for western blot analysis. The results indicated that immunoprecipitation with the antiserum, but not with the preimmune serum, still produced a predominant 105 kDa band. Again, this band was observed only on the surface of BL3 cells but not on that of EL4 T-cells, 32D myeloid progenitor cells or 3T3 fibroblasts.

Treatment with N-glycosidase F (BMB) confirmed that gp105 is indeed a glycoprotein. Glycosylation studies on gp105 were conducted according to the following procedure. After immunoprecipitation, the protein-Ab-protein A-agarose complex was resuspended with 6 mM Tris-HCl, pH 6.8 and 0.2% SDS, boiled for 5 min and spun for 2 min at room temperature. The supernatant was mixed with equal volume of 2× glycosidase buffer, which contains 200 mM sodium phosphate buffer (pH 6.6), 50 mM EDTA (pH 7.5), 2% Triton X-100, 0.1% SDS and 300 mM 2-mercaptoethanol. The mixture was incubated with 0.4 units of N-glycosidase F (BMB, Cat. No. 1365169) in a total reaction volume of 22 $\mu$l for 12–20 hrs at 37° C. Next, another 20 $\mu$l of 2× sample buffer as in western blot analysis was added to each sample. The samples were then boiled for 3 min before they were subjected to gel electrophoresis, which was done according to the procedure for western blot analysis.

After treatment with 0.4 units of N-glycosidase F overnight at 37° C., a predominant band with a molecular weight of 85 kDa in the immuno-precipitates was observed, indicating that the size of the unprocessed protein is 85 kDa and its glycosylated form is 105 kDa. While it remains unknown whether gp105 contains O-linked sugar moieties, gp105 is not autophosphorylated on tyrosine residues, suggesting that it does not contain tyrosine autophosphokinase activity.

Various molecules are known to be present on hematopoietic stem cells, and have been used for various analyses and purification of hematopoietic stem cells. These molecules, however, are distinguishable from gp105. As few as 100 Thy-1$^+$, Lin$^-$, Sca-1$^+$ cells can rescue 95% of lethally irradiated recipients. In contrast to gp105, Thy-1 and Sca-1 have molecular weights of 30 kDa and 8 kDa under non-reducing conditions, and 30 kDa and 18 kDa under reducing conditions, respectively.

A CD34 antigen has also been found on human hematopoietic stem cells. Its murine counterpart has been biochemically characterized to have a molecular weight ranging from 90–110 kDa, depending on the cell type. Its molecular weight therefore is similar to gp105. But CD34 is expressed in NIH/3T3 cells, PA6 stromal cells and M1 leukemic cells. As the western blot analysis and immunoprecipitation indicate, gp105 is not present in lysates of NIH/3T3 cells, 32D, FDC-P1 leukemic progenitor cells. Since the antiserum raised against BL3 cells contains polyclonal antibody, which recognizes probably several epitopes on the molecule, it is unlikely that gp105 is the murine CD34. In addition, hyperphosphylation of CD34 has been observed. In contrast, gp105 on BL3 cells is not phosphorylated under normal experimental conditions.

Hematopoietic stem cells also appear to express an important regulator, c-kit, which is a tyrosine kinase receptor for stem cell factor (SCF). SCF and c-kit have been used for enrichment of human and mouse stem cells. As RT-PCR and the MTT cell proliferation assay demonstrate, however, BL3 cells express neither c-kit nor SCF.

Another molecule on hematopoietic stem cells is AA4.1. This antigen has been shown initially to be on pre-B cells and later, on lymphomyeloid stem cells. The gene encoding for AA4.1 and its biochemical properties have not been characterized. A recent study indicates that, instead of its continuous presence on hemopoietic stem cells, AA4.1 expression may be related to a particular stage in cell cycle, suggesting that it is not specific for hemopoietic stem cells. BL3 cells are weakly positive with anti-AA4.1 and the positive cells are heterogeneous; this heterogeneity may also be related to cell cycle. By contrast, gp105 is present in abundance on BL3 cells, suggesting that these two molecules are not the same.

Flk-2 cDNA has been isolated from AA4.1 enriched hemopoietic stem cells and has been reported to be expressed with restriction in hemopoietic stem cells and progenitor cells. Independent cloning and analysis of flt-3, now considered the same gene as flk-2, suggest that the flt-3/flk-2 gene is expressed in several different types of cells and tissues. The gene encoding its ligand has been isolated and flt-3 has been shown to stimulate the proliferation of hemopoietic progenitor cells from fetal liver and adult bone marrows. Preliminary RT-PCR analysis suggests that both flt-3/flk2 ligand and receptor are not expressed in BL3 cells, which indicates that gp105 is unlikely to correspond to these molecules.

In addition, an antibody specifically directed against BL3 cells has been successfully raised. This antibody recognizes with high affinity and specificity gp105, which is present on BL3 cells in abundance. This antibody also can neutralize the activity of a factor that stimulates BL3 cell growth, and that is present in mitogen-stimulated spleen cells (SCM) or conditioned media of BL3 cells (BL3CM).

BL3CM was prepared according to the following procedure. BL3 cells were expanded until they were in log phase. They were then resuspended in fresh RPMI supplemented with 10% FCS at a concentration of 2 million cells per ml for 36 hrs. The spent medium was collected by centrifugation at 1,400 g at 4° C. Supernatant was stored at −20° C. until use. Spleen cell-conditioned medium was prepared as described in Wong et al., *PNAS* 86:7957–7960 (1989), which is incorporated herein by reference.

BL3 cell proliferation was assayed according to the following procedure. Exponentially growing BL3 cells were washed 3 times with RPMI supplemented with 2% FCS and 10 $\mu$g/ml gentamycin (R2 medium) and the cell concentration was usually adjusted to 4×10$^5$/ml in R2 medium. The cells were then mixed with serially diluted antiserum or conditioned medium preparations and deposited into individual wells of a 96-well microtiter plate. Usually 4–5 replicates for each experimental point were set up. Incubation was carried out in a 37° C. humidified 5% CO$_2$ incubator for 3–4 days. At the end of the incubation, the proliferation assay was performed. To do that, 10 $\mu$l of 5 mg/ml MTT (Sigma, 3(4,5-Dimethylthiazol-2-yl)-2,5- diphenyltetrazolium bromide) (Chung et al., *PNAS* 86:7957–7960 (1989)) was added into each well. The plates were incubated at 37° C. for another 4 hrs, then 100 μl of acid isopropanol was added to dissolve the formazan product of MTT reduction. The extent of coloring of each reaction mixture was then determined by a Microplate Reader with 570/630 dual wavelength (BioTek Instrument Inc., LE311).

That the addition of antiserum raised against BL3 cells to BL3 cell culture results in cell death indicates that neutralizing antibody that binds gp105 blocks the effect of an autocrine growth factor. Death of BL3 cells is due to the minimum culture conditions in which they were maintained, and to their unique properties of not able to respond to many different known growth factors. On the other hand, addition of the antiserum to clonogenic assay of cultures of fetal liver cells suggest that multipotent progenitor cells were only growth arrested, and upon replating in the absence of the antibody, they could still continue to develop multi-lineage colonies. In this culture condition, optimal growth stimulating amount of SCM, a source of many growth factors, was included. Fetal liver multilineage progenitor cells are known to respond to these factors, singly or in combination. Many of these factors can also maintain cell survival. Thus, using three different biological assays, specific stem cell effects were observed as a result of recognizing gp105 by the antiserum on their cell surface.

These data suggest that the hematopoietic regulatory factor in the conditioned media is either the ligand of gp105 or that gp105 is a subunit of a receptor to which the ligand binds. It is unlikely for two reasons that gp105 represents a general surface molecule totally independent from the ligand-receptor complex such that its recognition by the antibody inhibit cell growth in a dominant fashion. First, gp105 is present specifically on BL3 cells that retained many properties of hematopoietic stem cells and therefore could not be a general molecule such as one present in all types of cells for transmitting growth inhibition signals. Second, incubation of the antibody with BL3 cells results in cell death as discussed below. In contrast, incubation with fetal liver multipotential cells apparently resulted in growth arrest and not cell death. This pleiotropic effect is a characteristic suggestive of receptor-ligand molecules.

To show stimulatory activity, in conditioned media, of BL3 cells (BL3CM) or mitogen-stimulated spleen cells (SCM), BL3 cells in exponential growth phase, at a concentration of $2 \times 10^4$ in a final volume of 100 μl, were incubated with 10-fold dilutions of BL3CM or SCM. The dilutions were made in R2 medium (RPMI supplemented with 2% FCS). After 3 days of incubation, MTT (3(4, 5-diamethylthiazol-2-yl)-2, 5-diphenyltetrazolium bromide) assays were performend as described in Chung et al., *PNAS* 86:7957–7960 (1989).

Anti-BL3 specifically inhibited the proliferation of BL3 cells. BL3 cells in exponential growth phase, FDC-P1 cells or MM1 cells, at a concentration of $2 \times 10^4$ in a final volume of 100 μl, were incubated with 1:100 dilution of preimmune antiserum (Pre-S) or various dilutions (1:100 to 1:400) of anti-BL3 antiserum (Anti-S). The dilutions were made in R2 medium. MTT was added after 3 days of incubation, and the mixture incubated further for 4 hours. All readings of each cell line were normalized with those of the corresponding cells incubated with preimmune serum (pre-S), whose readings were expressed at 100% but whose actual average MTT readings were 0.147 for BL3, 0.541 for FDC-P1 and 0.903 for MM1 cells.

BL3 cells ($2.5 \times 10^4$) in a final volume of 100 μl containing R2, BL3CM or SCM, with or without pre-S or anti-S, were incubated for 4 days, after which MTT assays were performed, showing blockage of the stimulatory activity by anti-BL3 antiserum.

In addition to several important stem cell properties which they possess, BL3 cells do not respond to many cytokines that are known to have an effect on hematopoietic stem cells, either added to the culture singly or in combination. From the results discussed above, however, proliferation assay using BL3 cells as responding cells shows that BL3 cells respond to their own conditioned-medium prepared at high cell density. A stimulating activity is also present in the conditioned medium of mitogen-activated spleen cells. The response is dose-dependent. For unknown reasons, the activity detected in BL3 conditioned medium varied from batch to batch, whereas the activity from spleen cell conditioned medium was very consistent. Considering BL3 cells do not produce many known cytokines whereas mitogen-stimulated spleen cells do, it is possible that additional molecules are required to stabilize this hematopoietic regulatory factor(s).

The data above discussed also indicate that the addition of antiserum raised against gp105 can specifically inhibit the proliferation of BL3 cells, but not that of FDC-P1 myeloid progenitor cells and v-abl transformed MM1 mast cells. See Dexter et al., *Nature* 277:471–474 (1979); Chung et al., *PNAS* 88:1585–1589 (1991). Furthermore, the antiserum also can block the stimulatory activity found in mitogen-stimulated spleen cell conditioned medium. The inhibition also is dose-dependent, and complete inhibition can be achieved at a dilution of 1:100. In the presence of the antibody, BL3 cells maintain a survival curve not different from that of cells maintained at low cell concentration that is non-permissive for growth. This suggests that the antibody is not cytotoxic to BL3 cells because otherwise an accelerated rate of cell death would have been observed.

To determine whether growth and differentiation of multipotent hematopoietic progenitors isolated from normal fetal livers or bone marrows are affected in the presence of anti-gp105 antibody, an in vitro clonogenic assay was performed. Fetal liver cells from 12-day old mouse embryos ($6 \times 10^5$ cells in 0.1 ml R2 medium) were pre-incubated (2 hrs at 4° C.) with 0.1 ml of antiserum or preimmune serum at 1:10 or 1:100 dilutions, before they were plated in the semi-solid methylcellulose cultures containing 1% SCM, 1U/ml Epo (BMB) and 0.9% methylcellulose. Six to eight days later, the numbers and types of colonies were recorded as follows.

TABLE 1

Hematopoietic colony formation in the presence of anti-BL3 antiserum.

| | | No. of colonies / $3 \times 10^4$ cells plated | | | | | |
|---|---|---|---|---|---|---|---|
| | Dilution | BFU-E | CFU-M | E-mix | CFU-GM | others | Blast |
| Pre serum | 1:10 | 16 ± 1 | 49 ± 6 | 24 ± 4 | 25 ± 6 | 9 ± 6 | 0 |
| Anti-serum | 1:10 | 12 ± 2 | 68 ± 6 | 0 | 25 ± 2 | 5 ± 1 | 26 ± 6 |
| Pre serum | 1:100 | 14 ± 3 | 42 ± 2 | 25 ± 6 | 19 ± 2 | 8 ± 3 | 0 |
| Anti-serum | 1:100 | 14 ± 1 | 49 ± 2 | 26 ± 4 | 21 ± 4 | 10 ± 1 | 0 |

Duplicates were set up for each experimental point. The values shown are numbers±standard deviations of the means. Colony types were scored based on criteria set forth in Wong et al., *PNAS* 83:3851–3854 (1986), with the exceptions that "others" is defined as colonies of granulocytic or mast cell lineages, and "Blast" is defined as small colonies of less than 100 cells with blast cell phenotype. Similar results were obtained in three additional trials under identical conditions.

Strikingly, the typical multi-lineage E-mix colonies were not observed in cultures containing antiserum at 1:10 dilution, whereas they were present in cultures of preimmune serum. No difference in the numbers and types of colonies were observed in cultures of both preimmune and immune sera at 1:100. The total number of colonies in cultures with antiserum remained largely unchanged. In addition, small blast-like colonies could be observed in culture only with 1:10 dilution of the antiserum. Replating cells from 10 such colonies in the absence of the antibody yielded formation of 10 E-mix colonies, 2 CFU-M colonies and mast cell-like colonies. Therefore, the antibody can inhibit specifically the development of, but is not cytotoxic to, fetal liver cell-derived multi-potent progenitor cells in vitro.

CFU-S-forming cells are multi-potent hematopoietic progenitors capable of reconstituting lethally-irradiated recipient mice short-term. CFU-S spleen-focus assays were performed as described in Wong et al. (1994), supra, using donor adult bone marrow cells, with or without treatment of antibody plus complement. In the first experiment, bone marrow cells ($20\times10^6$ cells/ml), which were obtained from femurs of 7-week old C57BL/6 females, were incubated (45 min at 37° C.) with 15 µg/ml preimmune serum or purified anti-gp105 antibody at predetermined concentrations in the presence of 1:15 diluted low-toxin rabbit complement. Cells recognized by the antibody are lysed by complement. After viability check by trypan blue exclusion, $1\times10^5$ live cells in 0.5 ml R2 medium were injected into each lethally irradiated mouse (each received 10 cGy delivered by a $^{137}$Cesium source irradiator). Spleens of recipients were removed 13 days post-transplantation, fixed in Bouin's solution, and CFU-S colonies were scored. In the second experiment, 8-week old BALB/C females were used according to the same conditions as the first experiment with the exception of the amounts of antibody.

TABLE 2

Reduction of CFU-S after treatment with anti-gp105 and complement.

| Treatment | No. of CFU-S/ recipient | No. CFU-S Mean + SD |
|---|---|---|
| Exp. 1 | | |
| + anti-BL3 | 6,13,6,8,7,5 | 7.5 ± 2.9 |
| − anti-BL3 | 15,13,20,17,19 | 17.0 ± 2.7 |
| Exp. 2 | | |
| 50 µg/ml anti-BL3 | 4,4,5,5 | 4.5 ± 0.6 |
| 12.5 µg/ml anti-BL3 | 10,9,13,6,8 | 9.2 ± 2.6 |
| 50 µg/ml Pre-IgG | 17,16,18,14,16 | 16.2 ± 1.5 |
| 12.5 µg/ml Pre-IgG | 16,16,17,15 | 16.0 ± 0.8 |

In two experiments, there was a consistent reduction in the number of CFU-S foci in recipient spleens of bone marrow cells treated with the antiserum, compared with those treated with no serum or preimmune antiserum. The reduction was proportional to the amount of antibody used.

Antibody raised against BL3 cells was used to derive a BL3-derived λgt11 cDNA phage library by Lambda gt11/EcoR1/CIAP-Treated Vector Kit (Stratagene, La Jolla, Calif.), the written instructions of which are herein incorporated by reference. Identification of positive clones was performed by picoBlue Immunoscreening Kit (Stratagene, La Jolla, Calif.), the written instructions of which are herein incorporated by reference. Nucleotide sequence analysis of more than 1 kB DNA of a positive clone indicates that the gene encoding gp105 is unique but has homology to several genes encoding growth factor receptors or growth factors. In addition, sequence analysis of a positive clone expressing gp105 revealed the following partial nucleotide sequence (SEQ ID NO:1):

GAATTCTGAC ACCTCGTCTG TGCTCCATTT GGAAACTCTA CTAGCTGGGA TACCCAGACA GTCG- GAAGAA GCTTGCTCTG CTGCTCCCAG CGCAAGGGCA GACACGGAAT GGGAGGCTTA AAG- GAGAGAA ATACTGCTGA GCGTCGCTGG GCCTGCT- GCT GGGTCTGGGC TTGCTGCTGG GTGGGCTGAG CTGTTGAACC TGCTGAGGCT GTTGGACGGG TGGGGCCTGC TTGAGGCTGC TGGGCCTGCT GGGGCTGCTG GGCCTGCTGA GCCTGTGGAG CCT- GCTGGGC CTGCTGGACT GTGGCGCCTG CTGGGCT- GCT GGACCTGTGG CGCCTGCTGG GCTGTGGAGT CTGTGGGGCC TGTGGAGCCT GCGGGCCTGC TGGGCTTGCT GGGCCTGCTG GCTCGGACGT.

The positive clone characterized by the nucleotide sequence of SEQ ID NO:1 has been deposited, in accordance with the Budapest Treaty, in the American Type Culture Collection (ATCC). The deposited material will be made available to the public, irrevocably and without limitation, upon granting of a patent. In making this deposit, the inventors do not admit or imply that the deposit is required for compliance with 35 U.S.C. § 112.

Monoclonal antibodies against gp105 can be produced in various ways using techniques well-understood by those having ordinary skill in the art. Details of these techniques are described in *Antibodies: A Laboratory Manual,* Harlow et al. Cold Spring Harbor Publications, p. 726 (1988), which is hereby incorporated by reference. The monoclonal antibodies according to this invention are multiplied according to in vitro and in vivo methods well-known in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention may also be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane)

prior to injection. After one to three weeks, the desired monoclonal antibody is recovered from the body fluid of the mammal.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc., or they may be produced manually, using techniques well known in the art. See Geysen et al., *J. Immunol. Methods* 102:259–274 (1978), hereby incorporated by reference.

In another embodiment, the invention relates to a kit for detecting a hematopoietic regulatory factor that binds to gp105. This kit comprises the antibody of the present invention. The kit may also comprise a detectable label and a set of written instructions for using such a kit. Such a kit may comprise a receptacle being compartmentalized to receive one or more containers such as vials, tubes and the like, such containers holding separate elements of the invention.

In another embodiment, gp105 is used in a method of detecting in a sample a hematopoietic regulatory factor that binds gp105. This in vitro assay involves contacting a sample suspected of containing a hematopoietic regulatory factor that binds gp105 with detectably labeled-gp105. The hematopoietic regulatory factor is then detected. By "sample" is meant any cell culture medium or any body fluid or tissue, including blood, urine, saliva, spinal fluid, semen, peritoneal fluid, and tissue from any part of the body. Such assays may involve binding gp105 to a solid surface. Many methods for immobilizing biomolecules on solid surfaces are known in the art. For instance, the solid surface may be a membrane (e.g., nitrocellulose), a microtiter dish or a bead. The bound molecule may be covalently or noncovalently attached through unspecific bonding. The manner of linking a wide variety of compounds to various surfaces is well-known and well-documented in the literature. See, e.g., Chibata, *Immunological Enzymes,* Halsted Press (1978); Cuatvecasos, *J. Biol. Chem.* 245:3059 (1970), the respective contents of which are incorporated herein by reference.

In the assay of the present invention for detecting hematopoietic regulatory factors that bind gp105, gp105 is labeled by methods well-known in the art. A common method involves the use of radioisotopes such as $^3$H, $^{125}$I, $^{35}$S, $^{14}$C or $^{32}$P. Detection is accomplished by autoradiography. Non-radioactive labels include the covalent binding of biotin to the compound of the present invention. Biotin is then bound to an anti-ligand such as streptavidin, which is either inherently labeled or bound to a signal system, such as a detectable enzyme, a fluorescent or chemiluminescent compound.

Without further elaboration, it is believed that one skilled in the art can, using the preceding description, utilize the present invention to its fullest extent.

What is claimed is:

1. A method for preparing a composition enriched for hematopoietic stem cells, comprising the steps of (a) providing antibody that binds a protein encoded by the polynucleotide comprising the sequence set forth in SEQ ID NO:1, (b) immobilizing said antibody on a solid support such that said antibody retains its gp105-binding capability, then (c) bringing a mixed population of cells into contact with said antibody, wherein said mixed population contains hematopoietic stem cells, such that said stem cells adhere to said support, and (d) removing nonadherent cells, whereby a population enriched for hematopoietic stem cells remains adhered to said support.

* * * * *